(12) United States Patent
Yardimci et al.

(10) Patent No.: US 8,420,016 B2
(45) Date of Patent: Apr. 16, 2013

(54) MICROBIAL DEACTIVATION APPARATUS HAVING INTEGRATED ULTRASONIC DRYING SYSTEM

(75) Inventors: Ozlem Yardimci, Vernon Hills, IL (US); Alan M. Solomon, Mundelein, IL (US); Phillip S. Mallory, Cleveland, OH (US); David Jesurun, Cleveland, OH (US)

(73) Assignee: American Sterilizer Company, Mentor, OH (US)

( * ) Notice: Subject to any disclaimer, the term of this patent is extended or adjusted under 35 U.S.C. 154(b) by 786 days.

(21) Appl. No.: 11/749,326

(22) Filed: May 16, 2007

(65) Prior Publication Data

US 2008/0286178 A1 Nov. 20, 2008

(51) Int. Cl.
*B06B 1/00* (2006.01)
*A61L 2/00* (2006.01)
*B01F 11/00* (2006.01)

(52) U.S. Cl.
USPC .............................. 422/128; 422/20; 366/115

(58) Field of Classification Search .................. 422/128, 422/20; 366/115
See application file for complete search history.

(56) References Cited

U.S. PATENT DOCUMENTS

| 2,468,550 | A | * | 4/1949 | Fruth ................................. 8/159 |
|---|---|---|---|---|
| 3,327,401 | A | | 6/1967 | Stamos et al. ...................... 34/4 |
| 3,557,466 | A | | 1/1971 | Bodine ............................... 34/4 |
| 3,595,532 | A | * | 7/1971 | Doyle et al. ................... 366/111 |
| 3,641,680 | A | | 2/1972 | Candor et al. ...................... 34/1 |
| 3,750,306 | A | | 8/1973 | Rodwin et al. ................... 34/69 |
| 4,517,159 | A | * | 5/1985 | Karlson .......................... 422/20 |
| 4,639,078 | A | | 1/1987 | Sheem ....................... 350/96.21 |
| 4,929,975 | A | | 5/1990 | Shidara ......................... 354/317 |
| 5,105,557 | A | | 4/1992 | Vadasz et al. .................... 34/14 |
| 5,155,625 | A | | 10/1992 | Komatsu et al. .............. 359/512 |
| 5,171,387 | A | | 12/1992 | Wuchinich .................... 156/73.3 |
| 6,079,120 | A | | 6/2000 | Ekberg et al. ................... 34/401 |
| 6,662,812 | B1 | | 12/2003 | Hertz et al. ..................... 134/1.3 |
| 6,719,449 | B1 | * | 4/2004 | Laugharn et al. ............. 366/127 |
| 6,858,181 | B2 | | 2/2005 | Aoyagi ........................... 422/24 |
| 2002/0159917 | A1 | | 10/2002 | Swart et al. ..................... 422/20 |
| 2003/0029474 | A1 | * | 2/2003 | Gibbs et al. ....................... 134/1 |
| 2005/0025685 | A1 | * | 2/2005 | Selig et al. .................... 422/292 |
| 2005/0047957 | A1 | | 3/2005 | Nevin ............................. 422/20 |
| 2007/0131250 | A1 | * | 6/2007 | Classen ........................... 134/18 |
| 2007/0185385 | A1 | * | 8/2007 | Noguchi et al. .............. 600/132 |

FOREIGN PATENT DOCUMENTS

WO WO 2006001336 A1 * 1/2006

OTHER PUBLICATIONS

English Translation of Document No. WO 2006/001336 provided by the World Intellectual Property Organization: Noguchi, Endoscope Washing/Disinffecting System, Endoscope, and Endoscope Washing/Disinfecting Device, May 1, 2006.*

* cited by examiner

*Primary Examiner* — Kevin Joyner
(74) *Attorney, Agent, or Firm* — Kusner & Jaffe; Michael A. Centanni (57) ABSTRACT

A system for microbially deactivating articles, such as medical, dental, veterinary and mortuary instruments and devices. The system includes vibration means for producing ultrasonic waves to facilitate drying after the completion of a liquid microbial deactivation process.

20 Claims, 4 Drawing Sheets

MICROBIAL DEACTIVATION APPARATUS HAVING INTEGRATED ULTRASONIC DRYING SYSTEM

FIELD OF THE INVENTION

The present invention relates generally to disinfection or deactivation of articles, such as medical, dental, pharmaceutical, veterinary or mortuary instruments and devices, and more particularly, to a microbial deactivation system having means for ultrasonic drying following a chemical microbial deactivation process.

BACKGROUND OF THE INVENTION

Medical, dental, pharmaceutical, veterinary or mortuary instruments are routinely exposed to blood or other body fluids during various procedures. Following such procedures, a thorough cleaning and microbial deactivation of the instruments is required before subsequent use. Liquid microbial deactivation systems are now widely used to clean and deactivate instruments that cannot withstand the high temperature of a steam deactivation system. Liquid microbial deactivation systems typically operate by exposing the instruments to a liquid disinfectant or a deactivation composition, such as peracetic acid or some other strong oxidant. In such systems, the instruments to be cleaned are typically placed within a deactivation chamber of the deactivation system, or in a container that is placed within the deactivation chamber. During a deactivation cycle, a liquid disinfectant is then circulated through the deactivation chamber (and the container therein).

In order to maintain sterility of the instruments outside the deactivation system during storage, the instruments must be dried following completion of the deactivation cycle, thereby removing residual moisture from the instruments. The implementation of a separate "drying cycle" in the deactivation system significantly increases total processing time. Moreover, the liquid microbial deactivation system is unavailable for treatment of another load of instruments during the "drying cycle." Use of a separate drying device independent of the deactivation system also results in several problems. First, it may be difficult to maintain sterility while transferring instruments from the deactivation device to the drying device. The use of a separate drying device also requires additional expense to purchase the drying device, and additional space at the point of use.

The present invention overcomes the drawbacks of the prior art by providing a method and apparatus for ultrasonically drying articles in a liquid microbial deactivation system.

SUMMARY OF THE INVENTION

In accordance with a first aspect of the present invention, there is provided an apparatus for microbial deactivation of articles, the apparatus comprising: (a) a deactivation chamber dimensioned to receive a container enclosing at least one article to undergo microbial deactivation; (b) vibration means imparting vibrations to said container; (c) a fluid circulation system for circulating fluids through said deactivation chamber and inside said container; and (d) control means for controlling operation of said apparatus, wherein said control means activates said vibration means to produce vibrations having an ultrasonic frequency.

In accordance with another aspect of the present invention, there is provided an apparatus for microbial deactivation of articles, the apparatus comprising: a deactivation chamber dimensioned to receive a container enclosing at least one article to undergo microbial deactivation, said container including first vibration means for imparting vibrations to said container; a fluid circulation system for circulating fluids through said deactivation chamber and inside said container; and control means for controlling operation of said apparatus, wherein said control means activates said vibration means to produce vibrations having an ultrasonic frequency.

In accordance with yet another aspect of the present invention there is provided a method for removing moisture from inside an enclosed container following a liquid microbial deactivation process, said method comprising the steps of: (a) circulating dry air through the container; and (b) vibrating said container using vibration means that produce vibrations having an ultrasonic frequency.

One advantage of the present invention is the provision of a method and an apparatus for reducing drying time following a liquid microbial deactivation process.

Another advantage of the present invention is the provision of a method and apparatus for facilitating a drying process through the production of vibrations having an ultrasonic frequency.

These and other advantages will become apparent from the following description of an embodiment of the present invention taken together with the accompanying drawings and the appended claims.

BRIEF DESCRIPTION OF THE DRAWINGS

The invention may take physical form in certain parts and arrangement of parts, an embodiment of which will be described in detail in the specification and illustrated in the accompanying drawings which form a part hereof, and wherein.

DETAILED DESCRIPTION OF THE PRESENT INVENTION

Figure 1:
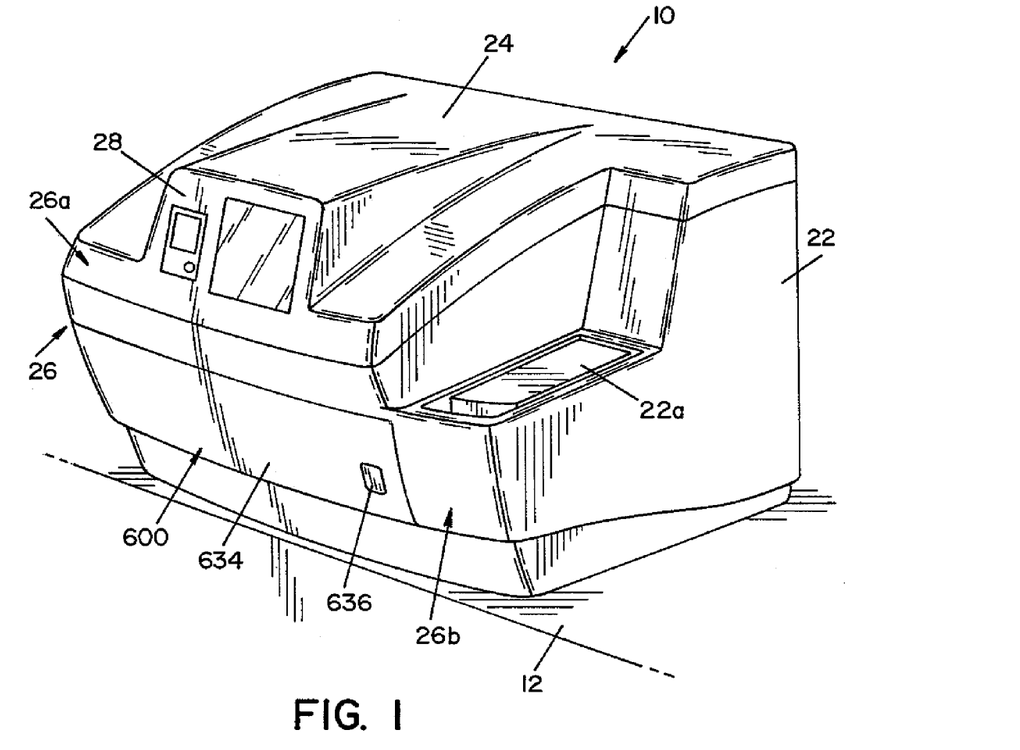
FIG. 1 is a perspective view of an automated reprocessor for microbially deactivating medical instruments, the reprocessor including an ultrasonic drying system according to an embodiment of the present invention.

Referring now to the drawings wherein the showings are for the purpose of illustrating a preferred embodiment of the invention only, and not for the purpose of limiting same, FIG. 1 shows an apparatus 10 for microbially deactivating articles, such as medical instruments and devices. It should be appreciated that while the present invention is illustrated as an integral part of apparatus 10, the illustrated apparatus is only exemplary of the type of apparatus into which the present invention may be integrated. In this regard, it is contemplated that the present invention may be used in connection with other microbial deactivation apparatus to facilitate drying following a liquid microbial deactivation process.

Apparatus 10 is designed to rest upon a table or countertop 12, as illustrated in FIG. 1. Countertop 12 in and of itself forms no part of the present invention. Apparatus 10 includes a housing structure 22 containing the operative components of apparatus 10. Housing structure 22 has an upper surface 24 that slopes generally downward toward a front face 26. Front face 26 has an upper section 26a and a lower section 26b. Upper section 26a includes a display panel 28.

A small, rectangular access panel 22a is formed in housing structure 22. In the embodiment shown, access panel 22a is formed to the right side of display panel 28 in a recess formed in housing structure 22. Access panel 22a is movable between a closed position, shown in FIG. 1, and an opened position, shown in FIG. 2. In its opened position, access panel 22a allows access to a chemistry-delivery system 400.

Figure 2:
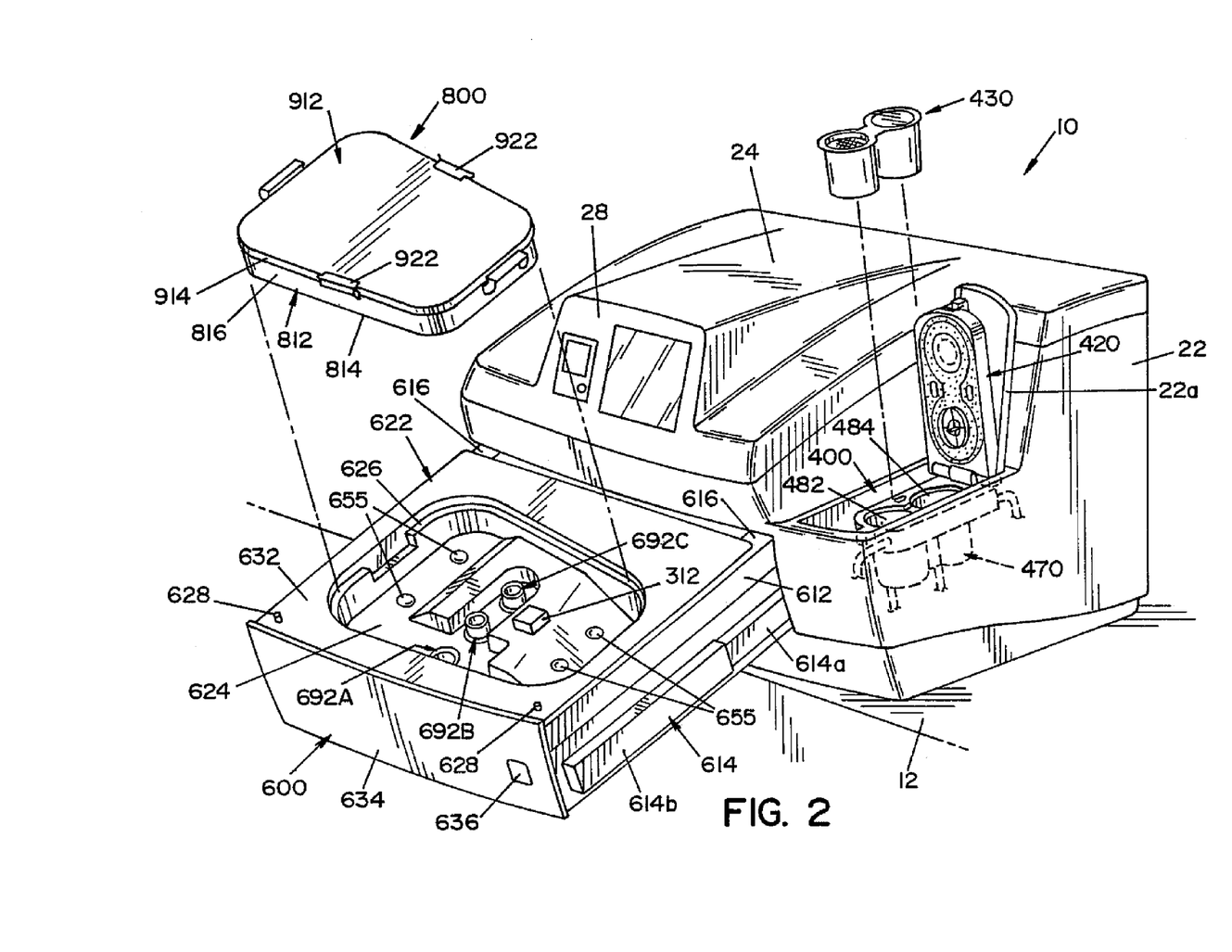
FIG. 2 is a perspective view of the reprocessor of FIG. 1, showing a movable drawer in an opened position and an instrument container removed therefrom, and also showing an access panel to a chemistry delivery system in an opened position and a chemistry container remover therefrom.

Referring now to FIG. 2, chemistry-delivery system 400 is comprised of a chemistry housing 470 and a movable lid 420 that attaches to chemistry housing 470. Chemistry housing 470 of chemistry-delivery system 400 includes two separate compartments 482, 484. Compartment 482 is dimensioned to receive chemistry-holding device 430 that contains a chemical reagent. Compartment 484 is dimensioned to receive a container that contains builder material to react with the chemical reagent in receptacle 482, thereby creating a microbial deactivation fluid (e.g., a peracetic acid solution). Lid 420 is designed to isolate the respective compartments 482, 484 when in a closed position.

A drawer assembly 600 includes a front face panel 634 that is coplanar with lower section 26b of front face 26 when drawer assembly 600 is in a closed position, as illustrated in FIG. 1. A drawer actuation button 636 is provided on front panel 634 of drawer assembly 600. Drawer assembly 600 is movable from a closed position, as shown in FIG. 1, to an opened position, as illustrated in FIG. 2. Drawer assembly 600 also includes a drawer tray 622 having a generally planar upper surface. A recessed cavity 624 is formed in tray 622, as illustrated in FIG. 2. Cavity 624 is dimensioned to receive a container 800 that encloses articles, such as medical instruments and devices. Container 800 is provided to receive the articles (e.g., medical instruments and/or devices) to be deactivated. Container 800 is dimensioned to be received within cavity 624. Drawer assembly 600 and container 800 are described in further detail below.

Figure 3:
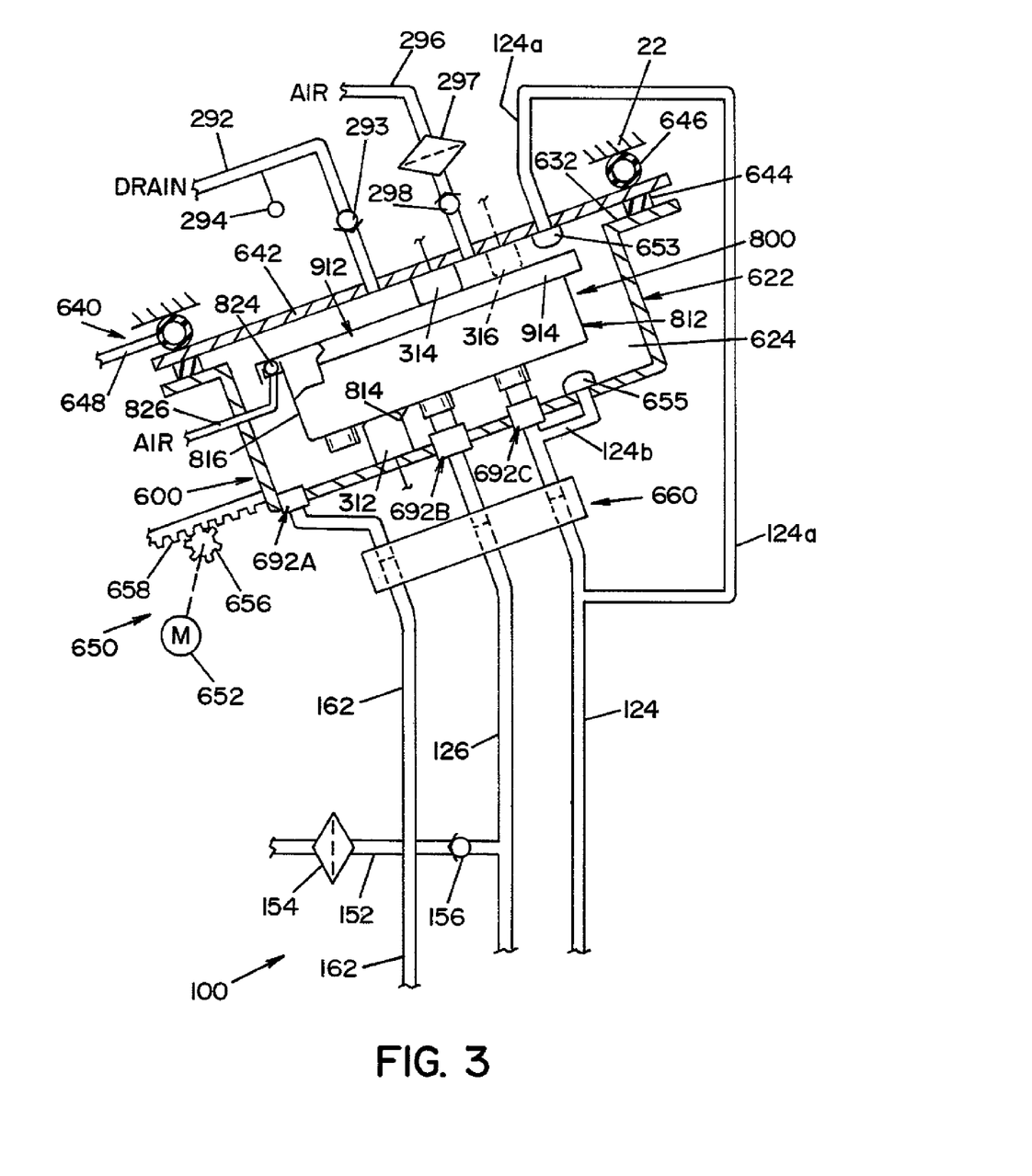
FIG. 3 is a partial schematic diagram of the reprocessor shown in FIG. 1, including a portion of the fluid circulation system.

Referring now to FIG. 3, a partial schematic diagram of apparatus 10 is shown. A more detailed schematic diagram is shown in U.S. patent application Ser. No. 11/714,046, filed Mar. 5, 2007, and fully incorporated herein by reference. As schematically illustrated, drawer assembly 600 includes a drive assembly 650, including a rack 658 and a pinion gear 656. Rack 658 is connected to drawer assembly 600 and is movable by pinion gear 656 that is driven by a motor 652. In FIG. 3, container 800 is shown disposed within cavity 624 defined by drawer tray 622. When drawer assembly 600 is in the closed position, as shown in FIG. 3, drawer tray 622 is disposed beneath plate 642. A static seal element 644 is disposed on the bottom side of plate 642 for contact with the planar portion of drawer tray 622. In this respect, static seal 644 is generally continuous about the periphery of cavity 624 in the drawer tray 622. An air-inflatable bladder 646 is provided on the top side of plate 642 to force plate 642 and static seal 644 into sealing engagement with the planar portion of drawer tray 622. Inflatable bladder 646 is disposed between the upper surface of plate 642 and housing structure 22 to force plate 642 into sealing engagement with drawer tray 622. An air line 648 fluidly connects inflatable bladder 646 with a source of air.

As schematically illustrated in FIG. 3, when container 800 is disposed within cavity 624 in drawer tray 622, container 800 is connected to a first fluid inlet line 124, a second fluid inlet line 126 and a return line 162 of a fluid circulation system 100. For the purpose of illustrating the present invention, only a portion of fluid circulation system 100 is shown in FIG. 3. Container 800 is also in communication with an air line 826 for inflating a seal 824 disposed between a tray 812 and a lid 912 of container 800.

To enable drawer assembly 600 and drawer tray 622 to move into and out of housing structure 22 of apparatus 10, fluid inlet lines 124, 126 and the return line 162 attached to drawer tray 622 are attachable and detachable to fluid circulation system 100 by means of a connector assembly 660.

When drawer assembly 600 is in a closed position and inflatable bladder 646 is activated to force static seal 644 into contact with the planar portion of drawer tray 622, a deactivation chamber is formed within apparatus 10, as schematically illustrated in FIG. 3. Fluid circulation system 100 provides microbial deactivation fluid to the deactivation chamber and is further operable to circulate the microbial deactivation fluid through the deactivation chamber, through container 800 and through instruments contained within container 800.

Fluids (e.g., water or a liquid microbial deactivation fluid) are supplied to container 800 and the deactivation chamber by first fluid inlet line 124 and second fluid inlet line 126. First fluid inlet line 124 includes a first branch section 124a that extends through the plate in drawer assembly 600 to communicate with cavity 624 defined by drawer tray 622. First branch section 124a is connected to spray nozzles 653 disposed on the lower, inner surface of plate 642. First fluid inlet line 124 also includes a second branch section 124b that is in communication with cavity 624. Second branch section 124b is connected to spray nozzles 655 disposed on the upper, inner surface of drawer tray 622.

A drain line (not shown) is also connected to first fluid inlet line 124. A valve (not shown) is disposed within the drain line to control the flow of fluid therethrough.

An air line 152 is connected to second fluid inlet line 126, as illustrated in FIG. 3. Air line 152 is connected to a source of dry air. A filter 154 is disposed within air line 152. A directional valve 156 is disposed within air line 152. Directional valve 156 is arranged to allow air to be forced into second fluid inlet line 126, but to prevent water or fluids within second fluid inlet line 126 from flowing toward the source of air.

Return line 162 is connected at a first end to connector assembly 660. The second end of return line 162 connects with a drain (not shown). The second end of return line 162 also connects with a recirculation line (not shown) that is connected with fluid inlet lines 124, 126. A valve (not shown) is disposed within return line 162 to control the flow of fluid therethrough.

A chemistry inlet line (not shown) connects chemistry-delivery system 400 to first fluid inlet line 124.

Referring now to drawer assembly 600 shown in FIG. 3, an overflow line 292 is connected to the inner plate so as to communicate with the deactivation chamber. The other end of overflow line 292 is connected to a drain source. A check valve 293 is disposed within overflow line 292 to allow the flow of fluid out of the deactivation chamber, but to restrict the flow of any fluid into the deactivation chamber through overflow line 292. A proximity sensor 294 is disposed within overflow line 292 downstream from directional check valve 293 to indicate when fluid is flowing therethrough. A make-up air line 296 is also connected to the deactivation chamber, as schematically illustrated in FIG. 3. A filter element 297 is disposed within make-up air line 296 to filter any air flowing into the deactivation chamber. In this respect, a directional check valve 298 is disposed within make-up air line 296 between filter element 297 and the deactivation chamber.

Directional check valve 298 allows the flow of air into the deactivation chamber, but restricts the flow of air or fluid out of the deactivation chamber.

Drawer assembly 600 will now be described in further detail with reference to FIGS. 2-4. Drawer assembly 600 includes two spaced-apart side panels 612. Each side panel 612 has a drawer slide 614 associated therewith. Drawer slide 614 has a first section 614a attached to housing structure 22 and a second section 614b attached to a side panel 612. Each side panel 612 has an inwardly extending flange 616 at the upper end thereof. Drawer tray 622 is dimensioned to rest upon inward-extending flanges 616. Drawer tray 622 is generally comprised of a flat panel having cavity 624 formed therein. Cavity 624 has a predetermined contour dimensioned to receive container 800. A ledge 626 is formed about the peripheral edge of cavity 624 to receive container 800. Drawer tray 622 is attached to inwardly extending flanges 616 of side panels 612 by conventional fasteners 628. Drawer tray 622 has a flat upper surface 632 that surrounds cavity 624. Front face panel 634, best seen in FIGS. 1 and 2, is attached to side panels 612. Control button 636, for controlling movement of drawer assembly 600, is mounted to front panel 634.

As shown in FIG. 3, a drawer sealing assembly 640 is disposed above drawer tray 622. Drawer sealing assembly 640 includes plate 642 that is disposed above drawer tray 622. The dimensions of plate 642 generally correspond to the dimensions of drawer tray 622. Static seal 644 is disposed on the lower surface of plate 642. Static seal 644 is disposed about the periphery of cavity 624 in drawer tray 622, so as to engage flat upper surface 632 of drawer tray 622. As indicated above, inflatable bladder 646 is disposed between plate 642 and housing structure 22. An air line 648 is connected to bladder 646 to inflate and deflate the same. When inflated, air bladder 646 is operable to force plate 642 downward toward drawer tray 622, wherein static seal 644 engages upper surface 632 of drawer tray 622 to form a seal about cavity 624 formed therein. When plate 642 is sealed against surface 632 of drawer tray 622, cavity 624 within drawer tray 622 defines a sealed deactivation chamber.

Overflow line 292 and make-up air line 296 are attached to plate 642 and extend therethrough. In this respect, when plate 642 is in a sealing position against drawer tray 622, overflow line 292 and make-up air line 296 are in communication with the deactivation chamber defined between plate 642 and drawer tray 622.

Connector assembly 660 is provided to allow the lines from fluid circulation system 100 to be connected to, and disconnected from, drawer assembly 600, so as to allow the opening and closing of drawer tray 622. Connector assembly 660 is comprised of a manifold section (not shown) that is mountable to drawer tray 622 and is movable therewith, and a platen section (not shown), that is movable into and out of engagement with the manifold section.

Figure 4:
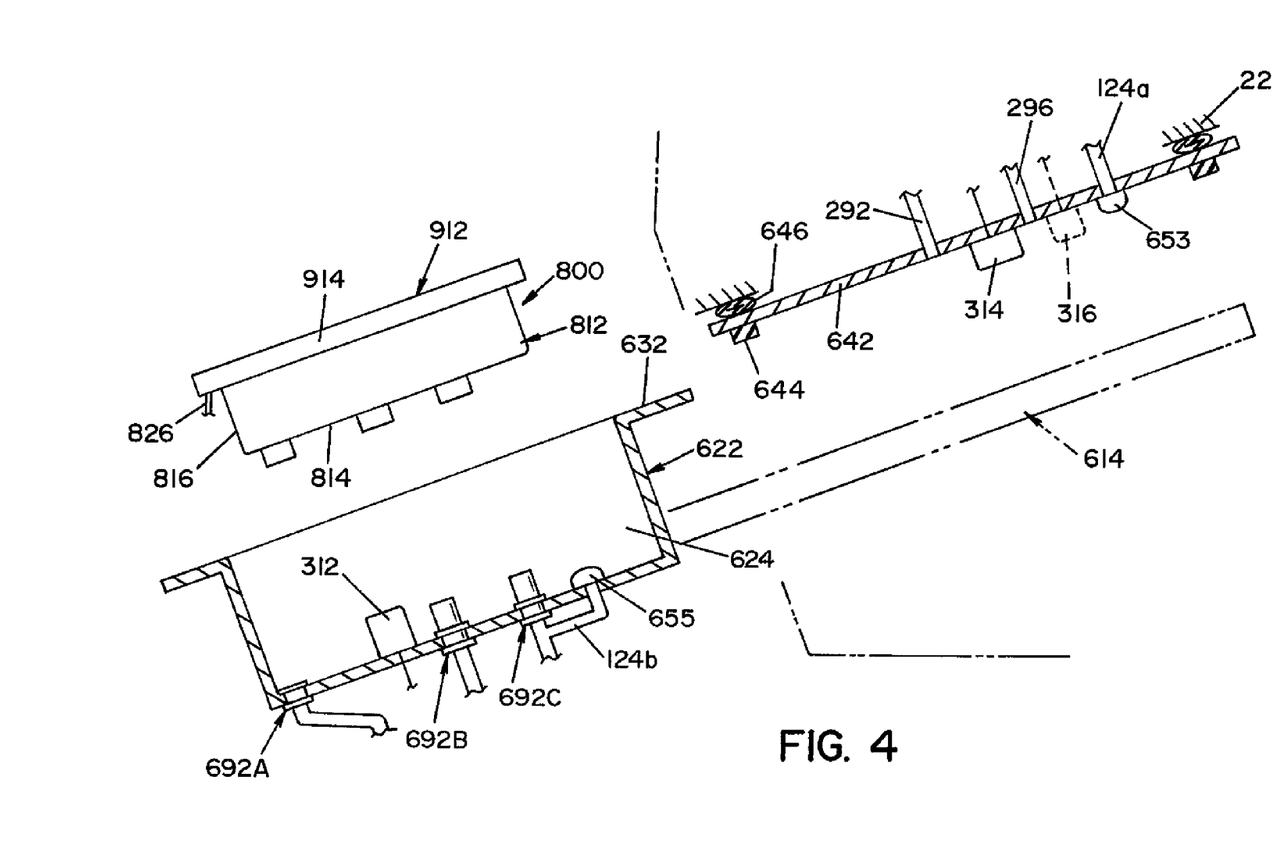
FIG. 4 is a partial schematic diagram of the reprocessor shown in FIG. 1, showing the movable drawer in the opened position and the instrument container removed therefrom.

Inserts 692A, 692B, 692C, are disposed in drawer tray 622, as best seen in FIG. 4. In the embodiment shown, insert 692A is a drain insert and inserts 692B, 692C, are connector inserts. Each insert 692A, 692B, 692C is a tubular structure having a closed lower end and an opened upper end.

In accordance with the present invention, one or more vibration means are located within the deactivation chamber defined by plate 642 and drawer tray 622. In the illustrated embodiment, the vibration means take the form of a device that vibrates at an ultrasonic frequency. By way of example, and not limitation, the vibration means takes the form of a piezoelectric transducer (PET). Other contemplated vibration means include, but are not limited to, magnetic coil actuators, pneumatically or hydraulically driven actuators, magnetorestrictive or capacitive actuators, and the like. An embodiment of the present invention will be described with reference to a vibration means in the form of a PET.

As well known, piezoelectric transducers include piezoelectric crystals that convert electrical energy into vibrational mechanical energy. When piezoelectric crystals are subjected to an externally applied voltage, the crystals change shape by a small amount. As a result, piezoelectric transducers can convert ultrasonic frequency voltages to ultrasonic waves or vibrations. In accordance with the present invention, the ultrasonic vibrations produced by piezoelectric transducers are transferred to the residual liquid water droplets and films within container 800 to facilitate drying. The ultrasonic vibrations promote uniform dispersion of residual liquid water, thereby increasing the surface area of the same. Dispersion of the residual liquid water in this manner facilitates a phase change of the residual water to a vapor. The ultrasonic vibrations produced by piezoelectric transducers also facilitate the conversion of liquid water into a fine mist.

In the illustrated embodiment of the present invention shown in FIGS. 2-4, a first piezoelectric transducer (PET) 312 is located on the upper, inner surface of drawer tray 622, and a second piezoelectric transducer 314 is located on the lower, inner surface of plate 642. PETs 312 and 314 are dimensioned such that they contact the outer surface of container 800 when container 800 is sealed within the deactivation chamber. In this regard, PET 312 contacts the lower surface of bottom wall 814 of tray 812 to impart vibrations thereto. Likewise, PET 314 contacts the upper surface of lid 912 to impart vibrations thereto. It should be understood that the vibration means may have alternative locations external to container 800, including locations inside and outside the deactivation chamber.

According to an alternative embodiment of the present invention vibration means are directly integrated into container 800. In this regard, container 800 is adapted to include vibration means as a component of tray 812 and/or lid 912. For example, vibration means may be integrated into bottom wall 814 of tray 812. The vibration means directly integrated into container 800 may be substituted for the vibration means located external to container 800 (as described above), or may supplement the vibration means located external to container 800.

A system controller (not shown) is programmed to control the operation of components of apparatus 10. The system controller receives data signals from devices (e.g., sensors), and transmits control signals to devices, such as motors, valves, vibration means and display units. The system controller may take the form of a microprocessor or a microcontroller.

Referring now to FIGS. 2-4, container 800 is best seen. Container 800 is generally comprised of a tray 812 and a lid 912 that is attachable to tray 812. Tray 812 is generally cup-shaped and has a bottom wall 814 and a continuous side wall 816 that extends about the periphery of bottom wall 814 to one side thereof. Bottom wall 814 and side wall 816 define a cavity in which articles, such as medical instruments, devices or other items to be deactivated, are to be inserted.

The upper edge of side wall 816 is shaped to define a channel dimensioned to receive a continuous, flexible seal 824. In the embodiment shown, seal 824 is an inflatable seal. An air conduit 826, schematically illustrated in FIG. 3, communicates with seal 824 by means of a fitting (not shown) that is mounted to container 800.

Lid 912 is generally a flat, planar element that is shaped to cover and enclose the opened, upper end of tray 812. Lid 912 includes a downward-extending flange 914 that extends about the periphery of lid 912 and is dimensioned to capture the upper edge of side wall 816.

A locking device 922 is provided to secure lid 912 to tray 812. In the embodiment shown, locking device 922 is an elongated, channel-like element that is pinned at one end to tray 812. The channel defined in the locking device 922 is dimensioned to capture the upper edge of tray 812 and lid 912.

Apparatus 10 shall now further be described with reference to the operation thereof. One or more articles to be deactivated, such as medical, dental, pharmaceutical, veterinary or mortuary instruments or devices, are loaded into container 800. Container 800 can accommodate numerous types of medical instruments and devices. Once the articles have been properly positioned within tray 812, lid 912 is placed over tray 812 and is locked into position, using locking device 922 on tray 812. With the articles to be microbially deactivated positioned within container 800, an operator opens drawer assembly 600 of apparatus 10 to allow container 800 to be placed within drawer tray 622.

A deactivation cycle for apparatus 10 includes a number of specific phases (i.e., preparation phase, system-seal phase, fill phase, circulation phase, chemistry-generation phase, exposure phase, and drain phase) that shall now be generally described.

Preparation Phase

During a user-preparation phase, drawer assembly 600 of apparatus 10 is movable between a closed position shown in FIG. 1 and an open position shown in FIG. 2 by manual manipulation of control button 636 on front panel 634. In preparation for a deactivation cycle, container 800 with the articles to be deactivated is placed within drawer tray 622 in drawer assembly 600. As illustrated in the drawings, cavity 624 in tray 622 and the shape of container 800 are such that container 800 may be placed within cavity 624 in only one orientation. With container 800 placed within drawer tray 622, drawer assembly 600 is moved to a closed position, using drawer control button 636.

During this user-preparation phase, chemistry-holding device 430 is inserted within the chemistry-delivery system 400. To this end, access panel 22a on housing structure 22 is moved to an open position to expose lid 420 of chemistry-delivery system 400. Lid 420 is unlatched and opened to expose compartments 482, 484 in chemistry-delivery system 400. Chemistry-holding device 430 is inserted within housing 470. Thereafter, lid 420 is closed and latched.

System-Seal Phase

With container 800 within drawer tray 622 of drawer assembly 600 and drawer assembly 600 in a closed position, a deactivation cycle may be initiated. A first phase of the deactivation cycle is a system-sealing phase, wherein air is applied to inflatable bladder 646 above plate 642. Inflating bladder 646 forces static seal 644 on plate 642 down into engagement with the planar surface of drawer tray 622, thereby forming a complete seal around cavity 624 in drawer tray 622, and forming a sealed, deactivation chamber containing container 800. Bladder 646 is maintained in an inflated state throughout the deactivation cycle.

Fill Phase

After bladder 646 has sealed container 800 within the deactivation chamber, a fill phase is initiated. Incoming water enters fluid circulation system 100 and proceeds to fill fluid circulation system 100, the deactivation chamber, and container 800.

The incoming water is under pressure from an external source and forces water into fluid circulation system 100, the deactivation chamber, and container 800. As a result of water entering the apparatus 10, air within the system is forced toward overflow line 292 that is preferably disposed at the highest point of apparatus 10. Directional check valve 293 allows air and water to exit the deactivation chamber. The presence of water flowing through overflow line 292 is sensed by proximity sensor 294. Water flowing through drain line 292 is indicative that apparatus 10 is filled. The system controller then stops the flow of water into apparatus 10.

Circulation Phase

Once apparatus 10 is filled with water, the system controller initiates a circulation phase to circulate water throughout fluid circulation system 100. During the circulation phase, water is circulated throughout fluid circulation system 100, including the deactivation chamber and container 800.

The purpose of the circulation phase is to achieve the proper fluid temperature to deactivate the articles located in container 800. At periods throughout the fill phase and the circulation phase, a heater may be activated to increase the temperature of the water flowing throughout the system to maintain a desired fluid temperature.

Chemistry-Generation Phase

Following the circulation phase, water flows through chemistry-delivery system 400 to produce a liquid microbial deactivation fluid.

Exposure Phase

During the exposure phase, the microbial deactivation fluid formed in the chemistry-generation phase is conveyed throughout fluid circulation system 100. The microbial deactivation fluid flowing through first and second fluid inlet lines 124, 126 flows into the deactivation chamber and into container 800 therein. The deactivation fluid flowing into container 800 is sprayed through spray nozzles around the exterior of the articles (e.g., medical instruments and devices) within container 800. Deactivation fluid circulates through the deactivation chamber formed by drawer tray 622 and plate 642 and flows out of the deactivation chamber to return line 162. Similarly, fluid flows out of container 800 through a return conduit to return line 162. During the exposure phase, deactivation fluid is circulated throughout fluid circulation system 100 and through the deactivation chamber and container 800 for a predetermined period of time. The circulation time is sufficient to decontaminate articles within container 800 and to decontaminate the components and fluid conduits of fluid circulation system 100.

Drain Phase

After a predetermined exposure period, the system controller initiates a drain phase. The drain phase is comprised basically of two steps. During the drain phase, valves to chemical-delivery system 400 are closed to prevent flow thereto. Valves in the drain lines are opened. Pumps continue to operate for a predetermined period of time, forcing the deactivation fluid in the deactivation chamber and container 800 out through the drain lines. At the same time, valves are opened to allow water to enter the system and flush chemistry-delivery system 400. Water entering chemistry-delivery system 400 is drained from fluid circulation system 100 through a drain line.

After a predetermined period of time sufficient to allow flushing of chemistry-delivery system 400 and after a period sufficient to allow draining of most of the fluid from fluid circulation system 100, the pumps are deactivated. Valves are closed to stop the flow of water to chemistry-delivery system 400.

A drying process is commenced by releasing a source of filtered, dry, pressurized air into the chemistry-delivery system 400. The dry air blows the remaining water within chemistry-delivery system 400 out through a drain line. Similarly, pressurized, dry air is applied to air line 152 and, thus, is conveyed through the lower portion of fluid circulation system 100 to blow out remaining fluid within the internal passages of instruments in container 800. The pressurized, dry air may be heated to facilitate the drying process. For example, the air may be heated to a temperature in the range of about 25° C. to about 190° C. The preferred heating temperature will be a temperature that does not cause damage to the instruments.

In accordance with the present invention, first piezoelectric transducer (PET) 312 and second piezoelectric transducer (PET) 314 are activated by the system controller during all or part of the drain phase to produce ultrasonic waves. PETs 312 and 314 facilitate the drying process, as will be described in detail below.

Once the drain phase has been completed, an indication is provided on the display panel 28 of housing structure 22. At that time, the air pressure to bladder 646 is removed to allow retraction of plate 642 and static seal 644 from the surface of drawer tray 622. Drawer assembly 600 may then be moved to an open position by pressing drawer-activation button 636. With drawer assembly 600 in an open position, container 800 can be removed from drawer tray 622. Since the fluid connections are in a closed position when container 800 is removed from drawer tray 622, microbial decontamination of the interior of container 800 is prevented.

As discussed above, PETs 312 and 314 convert voltages to vibrations having an ultrasonic frequency. Since PETs 312 and 314 are in contact with surfaces of container 800, container 800 is ultrasonically vibrated. The ultrasonic waves are transferred to liquid water inside container 800, including liquid droplets and films on the articles located therein. The ultrasonic waves promote dispersion of residual liquid water and the conversion of dispersed liquid water into a fine water mist. Increased dispersion of residual liquid water contributes to faster drying due to increased surface area of residual liquid water available for phase change. The dispersion of the liquid water also facilitates draining of liquid water from container 800. The fine water mist is more easily removed from container 800 by the dry air circulating therethrough. As a result of the foregoing, the drying time required for removing residual water from container 800 and the articles located therein is reduced.

The ultrasonic waves introduced into container 800 by PETs 312, 314 are also transferred to the air particles inside container 800. Ultrasonic vibration of the air particles facilitates the drying process by creating pressure waves (i.e., pulsating air). As the ultrasound pressure increases, molecular vibrations become more intense. As a result air particles in the field of the ultrasonic vibrations are displaced in harmony with the ultrasonic wave propagation, thus causing acoustic or turbulent flows within the volume of container 800 and near surfaces of container 800, thereby enhancing the drying process. In addition, ultrasound waves make ambient gas vibrate above the surface of porous materials, and acoustically create flows that carry moisture molecules away from the porous material. As a result, moisture removal from porous materials is promoted.

The use of ultrasonic waves in combination with a conventional drying processes reduces drying times, thereby allowing an apparatus for microbial deactivation to complete multiple consecutive microbial deactivation cycles within a shorter period of time.

In accordance with an alternative embodiment of the present invention, an ultrasonic receiver may also be mounted adjacent to the outer surface of container 800 in order to measure the rate of attenuation of the ultrasonic wave produced inside container 800 by the vibration means (e.g., PETs 312 and 314). In this regard, attenuation of the ultrasonic waves inside container 800 may be used to determine whether the drying process has been completed. As illustrated in FIGS. 3 and 4, an ultrasonic receiver 316 may be located on the lower, inner surface of plate 642. It is also contemplated that the ultrasonic receiver may be located on the upper, inner surface of drawer tray 622.

The system controller records a wave profile when the drying process or drain phase begins. The recorded wave profile is indicative of the ultrasonic wave produced inside container 800. Throughout the drying process new wave profiles are periodically recorded by the system controller. Each new wave profile is compared to the previously recorded wave profile. While the water content of container 800 is decreasing, the ultrasonic wave will attenuate. When no further moisture is being removed from container 800, no further attenuation of the ultrasonic wave will be observed. Once the system controller determines that the drying process has been completed, the drying cycle can be terminated by deactivating the supply of dry air.

Following completion of the drain phase described above, the deactivated articles may remain within container 800 and may be stored for future use, with the articles in container 800 remaining in a microbially deactivated environment. In this respect, container 800 may be inserted into a compartment of a storage cabinet, wherein connections on the bottom of container 800 engage and mate with connectors to allow dry, filtered air to be circulated into and out of the interior of container 800.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. An apparatus for microbial deactivation of articles, the apparatus comprising:
    a container for enclosing at least one article to undergo microbial deactivation;
    a deactivation chamber dimensioned to receive said container;
    a vibration element imparting ultrasonic vibrations to said container, wherein said vibration element is in contact with at least one surface of said container;
    a fluid circulation system for circulating fluids through said deactivation chamber and through the inside of said container, said fluid circulation system including a valve for controlling the removal of fluids from the inside of said container;
    a source of dry air connected with said fluid circulation system to circulate dry air through the inside of said container; and
    a controller for controlling operation of said apparatus,
    wherein said vibration element is active to introduce ultrasonic waves into said container while said source of dry air is fluidly connected to said fluid circulation system to circulate dry air through the inside of said container and said valve is in a position to allow air and residual liquid to exit from the inside of said container.

2. An apparatus as defined in claim 1, wherein said vibration element includes at least one piezoelectric transducer (PET).

3. An apparatus as defined in claim 1, wherein said vibration element includes first and second piezoelectric transducers, said first and second piezoelectric transducers in respective contact with surfaces of said container at opposite sides of said container.

4. An apparatus as defined in claim 1, wherein said vibration element includes at least one of the following: a piezoelectric transducer, a magnetic coil actuator, a pneumatically or hydraulically driven actuator, a magneto-restrictive or capacitive actuator.

5. An apparatus as defined in claim 1, wherein said deactivation chamber is defined by a tray having a bottom wall and a peripheral side wall, and a plate member moveable relative to said tray.

6. An apparatus as defined in claim 5, wherein said vibration element includes a vibrating device mounted to at least one of said tray and said plate.

7. An apparatus as defined in claim 1, wherein said vibration element is located within the deactivation chamber.

8. An apparatus as defined in claim 1, wherein said ultrasonic waves introduced into said container are transferred to air particles therein, thereby creating pressure waves inside said container.

9. An apparatus for microbial deactivation of articles, the apparatus comprising:
   a container for enclosing at least one article to undergo microbial deactivation;
   a deactivation chamber dimensioned to receive said container;
   a vibration element imparting ultrasonic vibrations to said container;
   a fluid circulation system for circulating fluids through said deactivation chamber and through the inside of said container, said fluid circulation system including a valve for controlling the removal of fluids from the inside of said container;
   a source of dry air connected with said fluid circulation system to circulate dry air through the inside of said container;
   a controller for controlling operation of said apparatus; and
   an ultrasonic receiver for generating a signal indicative of the frequency of ultrasonic waves detected by the ultrasonic receiver,
   wherein said vibration element is active to introduce ultrasonic waves into said container while said source of dry air is fluidly connected to said fluid circulation system to circulate dry air through the inside of said container and said valve is in a position to allow air and residual liquid to exit from the inside of said container, and
   wherein said controller receives said signal and is programmed to use said signal to determine whether a drying process has been completed by measuring the rate of attenuation of the ultrasonic waves produced inside said container by said vibration element.

10. An apparatus as defined in claim 9, wherein said controller is programmed to determine whether said drying process has been completed by recording a wave profile in association with said signal, and comparing each new wave profile to a previously recorded wave profile.

11. An apparatus for microbial deactivation of articles, the apparatus comprising:
   a container for enclosing at least one article to undergo microbial deactivation;
   first vibration means for imparting vibrations to said container;
   a deactivation chamber dimensioned to receive said container;
   a fluid circulation system for circulating fluids through said deactivation chamber and through the inside of said container;
   control means for controlling operation of said apparatus, wherein said control means activates said first vibration means to produce vibrations having an ultrasonic frequency; and
   an ultrasonic receiver for generating a signal indicative of the frequency of ultrasonic waves detected by the ultrasonic receiver,
   wherein said control means receives said signal and is programmed to use said signal to determine whether a drying process has been completed by measuring the rate of attenuation of the ultrasonic waves produced inside said container by said first vibration means.

12. An apparatus as defined in claim 11, wherein said first vibration means includes at least one piezoelectric transducer (PET).

13. An apparatus as defined in claim 11, wherein said first vibration means includes at least one vibration device.

14. An apparatus as defined in claim 11, wherein said first vibration means includes at least one of the following: a piezoelectric transducer, a magnetic coil actuator, a pneumatically or hydraulically driven actuator, a magneto-restrictive or capacitive actuator.

15. An apparatus as defined in claim 11, wherein said deactivation chamber is defined by a tray having a bottom wall and a peripheral side wall, and a plate member moveable relative to said tray.

16. An apparatus as defined in claim 15, wherein said apparatus includes second vibration means mounted to at least one of said tray and said plate.

17. An apparatus as defined in claim 11, wherein said apparatus includes second vibration means located within the deactivation chamber.

18. An apparatus as defined in claim 11, wherein said apparatus includes second vibration means in contact with an outer surface of said container.

19. An apparatus as defined in claim 11, wherein said control means is programmed to determine whether a drying process has been completed by recording a wave profile in association with said signal, and comparing each new wave profile to a previously recorded wave profile.

20. An apparatus as defined in claim 11, wherein said first vibration means is integrated into said container.

* * * * *